US007008229B2

(12) United States Patent
Stoller et al.

(10) Patent No.: US 7,008,229 B2
(45) Date of Patent: Mar. 7, 2006

(54) STAINLESS STEEL DENTAL CROWNS WITH A POLYESTER/EPOXY COATING

(75) Inventors: William J. Stoller, Lake Forest, CA (US); Shig Shiwota, Huntington Beach, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 192 days.

(21) Appl. No.: 10/121,941

(22) Filed: Apr. 12, 2002

(65) Prior Publication Data

US 2003/0194681 A1    Oct. 16, 2003

(51) Int. Cl.
*A61C 5/08* (2006.01)
(52) U.S. Cl. .................... 433/222.1; 433/218
(58) Field of Classification Search ............ 433/222.1, 433/218, 219, 202.1, 203.1, 208, 223, 212.1
See application file for complete search history.

(56) References Cited

U.S. PATENT DOCUMENTS

| | | | |
|---|---|---|---|
| 3,422,535 A | 1/1969 | Johnson | |
| 3,481,772 A | 12/1969 | MacNarin et al. | |
| 3,585,723 A | 6/1971 | Simor | |
| 4,503,169 A | 3/1985 | Randklev | |
| 4,568,606 A | 2/1986 | Hart et al. | |
| 4,668,193 A | 5/1987 | Burgess et al. | |
| 4,722,689 A | 2/1988 | Corbett | |
| 5,011,410 A | 4/1991 | Culler et al. | |
| 5,454,716 A | 10/1995 | Banerjee et al. | |
| 5,709,548 A | 1/1998 | Oxman et al. | |
| 5,998,495 A * | 12/1999 | Oxman et al. | 522/15 |
| 6,030,606 A | 2/2000 | Holmes | |
| 6,095,809 A | 8/2000 | Kelly et al. | |
| 6,106,295 A | 8/2000 | Wilson | |
| 6,142,775 A | 11/2000 | Hansen et al. | |
| 6,632,853 B1 * | 10/2003 | Alkemper et al. | 522/83 |

FOREIGN PATENT DOCUMENTS

| | | |
|---|---|---|
| EP | 434010 A1 | 3/1994 |
| EP | 434010 B1 | 3/1994 |
| JP | 79041631 | 12/1979 |
| JP | 56-77214 A | 6/1981 |
| JP | 56077214 | 6/1981 |
| JP | 58-169443 | 10/1983 |
| JP | 90038219 | 8/1990 |
| SU | 1139432 A | 2/1985 |
| WO | WO 00/20494 | 4/2000 |
| WO | WO 01/30304 | 5/2001 |
| WO | WO 01/30305 | 5/2001 |
| WO | WO 01/30306 | 5/2001 |
| WO | WO 01/30307 | 5/2001 |

OTHER PUBLICATIONS

"3M Prefabricated Crowns: User Guide" 3M Technical Service Publication No. 70-2008-7866-1, 8 pgs total (no month indicated, 1996).
Baker et al., "Retention of esthetic veneers on primary stainless steel crowns," *Journal of Dentistry for Children*, May-Jun.: 1996; 185-189.

(Continued)

*Primary Examiner*—Melba N. Bumgarner
(74) *Attorney, Agent, or Firm*—Sean J. Edman

(57) ABSTRACT

A dental crown that includes a stainless steel shell sized to cover a tooth portion of a patient and a polymeric coating including a polyester/epoxy hybrid composition.

20 Claims, 1 Drawing Sheet

OTHER PUBLICATIONS

Croll et al., "Preformed resin-veneered stainless steel crowns for restoration of primary incisors" *Quintessence International,* 1996; 27(5):309-313.

Croll et al., "Primary incisor restoration using resin-veneered stainless steel crowns," *Journal of Dentistry for Children,* Mar.-Apr.: 1998; 89-95.

DeLong et al., "Development of an Artificial Oral Environment for the Testing of Restoratives: Bi-axial Force and Movement Control" *J. Dental Research,* Jan. 1983; 62(1): 32-36.

"Gemtech, Inc—Frequently Asked Questions" available online at <http://www.gemtechpowder.com> 2 pgs.

Fuks et al., "Clinical performance of esthetic posterior crowns in primary molars: a pilot study," *Pediatric Dentistry,* 1999; 21(7):445-448.

"Pedo Pearls: Affordable cosmetic dentistry," Pedo Pearls Dental Crowns. Product Information Sheet [online] 1 pg. Pedo Pearls 2001 [retrieved on Oct. 23, 2001]. Retrieved from the Internet: <URL: http://www.pedopearls.com.index.html>.

"Pedo Pearls," Pedo Pearls Dental Crowns. Product Information Sheet [online] 1 pg. Pedo Pearls 2001 [retrieved on Oct. 23, 2001]. Retrieved from the Internet: <URL: http://www.pedopearls.com/images/ikitlg.jpg>.

"Pedo Pearls: Q & A," Pedo Pearls Dental Crowns Question and Answer. Product Information Sheet [online] 2 pgs. Pedo Pearls 2001 [retrieved on Oct. 23, 2001]. Retrieved from the Internet: <URL: http://www.pedopearls.com/faq.html>.

"Pedo Pearls: Contact," Pedo Pearls Dental Crowns Contact Page. Product Information Sheet [online] 1 pg. Pedo Pearls 2001 [retrieved on Oct. 23, 2001]. Retrieved from the Internet: <URL: http://www.pedopearls.com.contact.html>.

Liberto (Ed), *Powder Coating The Complete Finisher's Handbook,* The Powder Coating Institute, Title page, Publication page, and Table of Contents (no month indicated, 1994).

Liberto (Ed), "Powder Coating Materials," *Powder Coating The Complete Finisher's Handbook,* Second Edition, The Powder Coating Institute, Title page, Publication page, and Chapter 3 (pp. 12-19) (no month indicated, 1999).

Waggoner et al., "Failure strength of four veneered primary stainless steel crowns" *Pediatric Dentistry,* 1995;17(1):36-40.

Wickersham et al., "Color change and fracture resistance of two preveneered stainless-steel crowns after sterilization," *Pediatric Dentistry,* 1998: 20(5):336-340.

"Company Info," Datasheet [online]. Java Crowns, Inc., 2002 [retrieved on Aug. 30, 2002] Retrieved from the Internet: <URL: http://javacrown.com/company.htm>.

"Products," Datasheet [online]. Java Crowns, Inc., 2002 [retrieved on Aug. 30, 2002] Retrieved from the Internet: <URL: http://javacrown.com/products.htm>.

Product Information Brochure, "White Steel Crowns Information Sheet," White Steel Dental Products, Inc., Murphy, OR (no date available).

Pedo Pearl Information Sheet, Pedo Pearls Dental Products, Inc., Merlin, OR, 1 page (no date available).

Material Safety Data Sheet for Pearly Whites, 4 pages (Aug. 22, 2002).

* cited by examiner

STAINLESS STEEL DENTAL CROWNS WITH A POLYESTER/EPOXY COATING

BACKGROUND OF THE INVENTION

Preformed stainless steel crowns (SSCs) are still the preferred choice for whole or partial replacements of teeth. They are a very durable and reliable restoration for a tooth in need of complete coverage. Typically, stainless steel crowns are designed to provide long-term coverage of primary molar teeth and long-term provisional coverage of first permanent molar teeth.

Commercially available stainless steel crowns are preformed into an anatomically correct shape having a life-like height, contour, and occlusal surface. Dental composites provide an alternative, which resemble teeth, but lack the strength of preformed stainless steel crowns. Many patients, such as those with extensive caries, or those who have occlusions with deep anterior bites, or those who grind their teeth, generally need the strength of stainless steel crowns.

Stainless steel crowns are also desirable because they are made of a malleable material that allows the crown to be cut and trimmed to provide a comfortable bite on the occlusal surface of the opposite tooth. Furthermore, stainless steel crowns can be crimped around the base of the remaining portion of the tooth to provide a smooth, comfortable and secure fit.

Stainless steel crowns, however, have an unattractive appearance. Thus, there is a need for stainless steel dental crowns that have a more natural look with preferably a tooth-like color. Attempts have been made using resins, such as polyesters, epoxies, acrylics, and high-density polyethylene, to form an aesthetically pleasing veneer. Some veneers require the use of mechanical retention means, such as a screen mesh, on the facial side of a tooth as a foundation to which is attached the veneer. However, there is still a need for more durable aesthetic SSCs.

An aesthetic SSC is designed with several objectives in mind. One purpose is to hide the base material covering the natural tooth so that a more natural looking artificial tooth is seen. The aesthetic SSC also makes contact with other teeth or dental work, as well as food items placed in the mouth. Consequently, the preformed crown with the veneer or coating in place must be able to withstand great shearing stresses because of the contact with forces of occlusion.

SUMMARY OF THE INVENTION

The present invention provides stainless steel dental crowns having an outer surface at least partially coated with a coating that includes a polyester/epoxy hybrid composition. Preferably, the crowns, or at least an outer surface thereof, is composed of stainless steel, which is coated with the polyester/epoxy hybrid composition. The coated dental crowns possess enhanced aesthetics, particularly because the polymeric coating can be tooth-colored.

The coating can be a very thin layer that will remain adhered to the crown during the manipulation necessary for applying the crown to a tooth. Typically, the coating adheres to the malleable metal and does not peel or chip under normal use and mastication when the crown is cut and applied properly. The coating is preferably a polymeric coating that includes a polyester/epoxy hybrid composition, optional filler material (typically used to enhance durability), and an optional pigment (typically used to give the natural tooth color). As used herein, "a" or "an" mean "at least one" or "one or more" unless otherwise indicated.

The polymeric coating preferably is applied to at least a portion of a surface of a stainless steel crown by a powder coating process. The powder used to form the coating has a melting or softening temperature in a range that will not affect the integrity of either the polymeric coating or the stainless steel crown. The polyester/epoxy hybrid composition of the invention refers to a composition that includes a combination, e.g., a blend, of a polyester resin component and an epoxy resin component. As defined herein, the composition can include the resins as present in the starting coating powder (e.g., as dry particles) or in the final polymeric coating (e.g., as part of the surface coating resulting from melting and then solidifying and bonding the coated powder to the crown). It is to be understood that the melting process typically results in a curing (e.g., through cross-linking, for example) of the polyester and epoxy resins such that higher molecular weight polymers are formed in the polymeric coating. Therefore, the resins may have very different properties in the polymeric coating than in the starting coating powder.

The coated crowns are desirable because they do not detract from the patient's appearance as do the metal or partially metal devices. The optional pigment(s) included in the coating is matched to correlate to the color of a tooth and thereby blend in with the teeth in the patient's mouth. Preferably, the coated crowns are durable, particularly during crimping and trimming, and have extended wear times.

In one embodiment, the present invention provides a dental crown that includes a stainless steel shell (a term that is used herein to encompass fully stainless steel or partially stainless steel devices) sized to cover a tooth portion of a patient (whether the patient be human or animal, adult or child) and a polymeric coating covering at least a portion of the outer surface of the stainless steel shell, wherein the polymeric coating includes a polyester/epoxy hybrid composition.

In another embodiment, the present invention provides a dental crown that includes a stainless steel shell sized to cover a tooth portion of a patient and a polymeric coating covering at least a portion of the outer surface of the stainless steel shell, wherein the polymeric coating includes a polyester/epoxy hybrid composition, and wherein the coating is at least about 35 microns thick.

Preferably, the polymeric coating further includes a pigment (i.e., one or more pigments such as titanium dioxide, iron oxide, or mixtures thereof). Optionally, the polymeric coating can include a filler material (which can be a mixture of various particulate materials, but is typically silica, and more particularly silane-treated silica).

In a particularly preferred embodiment, the present invention provides a dental crown that includes a stainless steel shell sized to cover a tooth portion of a patient and a polymeric coating covering at least a portion of the outer surface of the stainless steel shell, wherein the polymeric coating includes a polyester/epoxy hybrid composition, a pigment, and a filler (i.e., filler material), and wherein the coating is at least about 35 microns thick.

The present invention also provides a method of coating a stainless steel crown. The method includes: providing a stainless steel shell sized to cover a tooth portion of a patient; providing a polyester/epoxy hybrid powder; and applying the powder to at least a portion of the outer surface of the stainless steel shell to form a polymeric coating. Preferably, the powder-coated crown is heated at a temperature and for a time sufficient to melt and fuse the particles to the stainless steel. Preferably, the powder has an average particle size of about 20 to about 100 microns. The coated crown produced by this process is also provided.

DETAILED DESCRIPTION OF PREFERRED EMBODIMENTS

Figure 1:
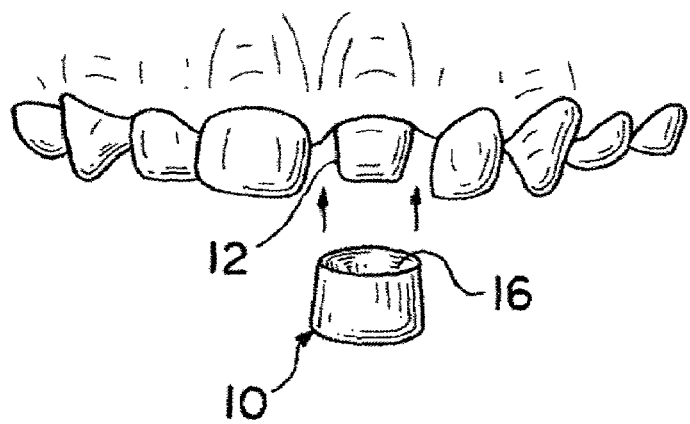
FIG. 1 illustrates where the preformed base stainless steel crown 10 of FIG. 1 is placed on a tooth 12 that is prepared to receive it.

A typical SSC is constructed from a preformed base material crown 10 composed of stainless steel, which is placed in the mouth to cover a prepared tooth 12 as shown in FIG. 1. The prepared tooth 12 is shown as having its surface ground away sufficient for the placement of the crown 10 thereon. The scale of the teeth shown and the crown 10 to be placed thereon is for ease of illustration and should not be considered to be at the correct scale. Furthermore, the portion of the tooth 12, which has been ground away, is also for illustration purposes only. As shown in FIG. 1, the base metal crown 10, which as shown for illustration purposes, is not a molar, and therefore can be pictured generally as a flattened bowl which is formed in the shape of a tooth with an open end 16 for placement over the prepared tooth 12. Proper tooth preparation includes removing all caries and proper shaping of the remaining natural tooth 12 to receive the SSC 10. Therefore, the prepared tooth 12 is typically left in place in the mouth so that its root provides anchor in the jaw for the SSC. An aesthetic SSC, however, also includes a coating containing a polyester/hybrid composition placed over the base metal 10. The SSC 10 shown in FIG. 1 is an anterior crown; however, it is to be understood that the present invention is applicable to both anterior and to posterior coated crowns as well.

Typically the crown is shaped to resemble the tooth that it replaces and is sized to fit comfortably over the portion of the tooth on which the dental procedure is being performed. The crown is trimmed so that the bottom edge of the crown meets the gum line in a comfortable manner approximating the placement of the tooth when the crown is applied. The crowns are manufactured in size and shapes to fit the various types of teeth. The stainless steel is malleable so it can be crimped around the base of the tooth and shaped on the occlusal surface to provide a comfortable bite with the opposing tooth. The hybrid polyester/epoxy coating is sufficiently adhered to the stainless steel that it does not chip or crack during such crimping process.

Figure 2:
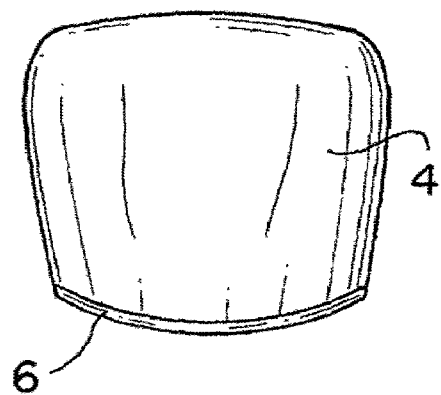
FIG. 2 is an elevational front (facial) view of an aesthetic SSC.
Figure 3:
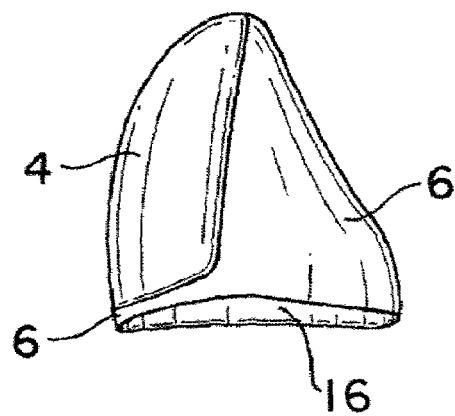
FIG. 3 is an elevational profile (interproximal) view of the aesthetic SSC of FIG. 2.

FIG. 2 shows a facial (frontal) view of an aesthetic SSC, showing a polymeric coating 4 and a thin margin of base metal 6 at the cervical (bottom) margins. Typically and preferably, the entire tooth is coated with a polymeric coating that includes a polyester/epoxy hybrid composition. However, if desired, only the facial surface of the crown can be covered with a coating 4 and the base metal 6 on the facial margin extends to the interproximal and the lingual (inside of mouth). This is shown in FIG. 3, which shows an interproximal (side) view of an aesthetic SSC.

Commercially available preformed stainless steel crowns can be obtained from 3M Company, St. Paul, Minn.. Other sources of preformed stainless steel crowns include Denovo, Baldwin Park, Calif.; Space Maintainer Laboratory, Van Nuys, Calif.; Masel, Philadelphia, Pa.; Rugby, Rockville Center, N.Y.; and, Sankin, Japan. Such preformed crowns can then be coated with a polymeric coating containing a polyester/epoxy hybrid composition to form the coated crowns of the present invention.

The preformed base metal in a SSC is typically constructed of cold rolled stainless steel. Prior to coating, the crown can be prepared to remove oil or other surface contaminants by vapor degreasing, alkaline cleaning, acetone cleaning, or ultra-sonic cleaning, for example, as needed. Surface oxides may be removed and surface activation can be accomplished by acid treatment or abrasive blasting, for example. Preferably, commercially available polished SSCs are cleaned with acetone prior to powder coating.

Typical stainless steel materials used to construct stainless steel crowns useful in the present invention include AISI-Types 304 and 305 stainless steel sheeting (based on the American Iron and Steel Institute Classification of Chromium-Nickel Stainless Steels). Such sheeting includes a metal alloy of iron, chromium, and nickel typically with small or trace amounts of manganese, carbon, titanium, aluminum, silicon, tantalum, and molybdenum.

A polymeric coating that includes a polyester/epoxy hybrid composition is sufficiently thin such that it possesses enough pliability so that it will crimp with the metal layer around the tooth portion to be protected, but sufficiently thick such that it will be durable enough to withstand typical chewing conditions throughout the life of the crown. The stainless steel crown is covered by a polymeric coating that is preferably at least about 35 micrometers (i.e., microns) thick, and more preferably, at least about 50 micrometers thick. Preferably, the polymeric coating is no more than about 100 micrometers thick, and more preferably, no more than about 75 micrometers thick.

The polymeric coating is pliable so that it does not peel or flake off during common crown manipulations, e.g., crimping and trimming, and is durable such that it resists wearing off and delaminating during long periods of wear in a patient's mouth. The hybrid polyester/epoxy-coated crowns, as shown in Examples 1–9 and 12–15, generally have little or no significant cracking or flaking upon crimping and trimming according to the procedures listed in the Examples Section. In contrast, crimping of an epoxy-coated stainless steel crown resulted in immediate and significant separation of the coating from the crown surface.

A polymeric coating that includes the polyester/epoxy hybrid composition preferably has a high gloss, and can be color-matched to the natural teeth. The polyester/epoxy hybrid composition of the invention includes a combination, preferably a blend, and more preferably a homogeneous blend, of a polyester resin component and an epoxy resin component. Coating powders, also commonly known as powder coatings, that include a polyester/epoxy hybrid composition are generally known as "hybrid" powders; whereas, coating powders that include only a polyester resin or only an epoxy resin are generally known as "polyester" powders or "epoxy" powders, respectively. "Resin" in the context of this invention means a synthetic polymer having repeating ester linkages (for polyesters) or repeating ether linkages (for epoxy polymers). Preferably, a polymeric coating that includes a polyester/epoxy hybrid composition is a coating formed by a conventional powder coating process that utilizes a powder including a polyester resin component and an epoxy resin component.

Coating powders that include a polyester/epoxy hybrid composition are typically thermosetting coating powders or powder coatings. Thermosetting coating powders are primarily composed of relatively high molecular weight solid resins and one of a variety of available crosslinkers. When applied to a substrate, e.g., a stainless steel crown, and heated to a molten state, the material will flow and typically chemically react (i.e., cure) to form higher molecular weight polymers in a network-like structure. These higher molecular weight polymers are in part responsible for imparting excellent physical properties (e.g., durability, resistance to wear, and flexibility) to the film-like polymeric coating. A further discussion of powder coating materials and their properties can be found in Chapter 3, "Powder Coating Materials," in Powder Coating, Second Edition, published by The Powder Coating Institute, 1999.

Coating powders that include polyester/epoxy hybrid compositions are available from a variety of sources, including Morton Powder Coatings, Reading, Pa. (CORVEL FDA WHITE 40-1242) and DuPont, Wilmington, Del. (Product No. 388170B (Light Ivory) and Product No. 388171B (Dark Ivory)). Preferably, coating powders that include polyester/epoxy hybrid compositions have an average particle size (i.e., the largest dimension of a particle, such as the diameter of a spherical powder) of at least about 20 microns, and more preferably at least about 40 microns. Preferably, the average particle size is no more than about 100 microns, and more preferably no more than about 60 microns. Preferred coating powders include about 20 percent by weight (wt-%) to about 40 wt-% polyester, and about 20 wt-% to about 40 wt-% epoxy, based on the total weight of the coating powder.

The starting coating powders used in the preparation of the present invention coated crowns preferably include tooth-color pigments and other materials to facilitate the incorporation and dispersion of these pigments into the powder. A tooth-colored pigment can be achieved, for example, by using a mixture of titanium dioxide and iron oxide. The titanium dioxide and iron oxide pigments can be used in varying amounts depending on the shade of tooth enamel desired to be reproduced. For example, about 20 wt-% to about 40 wt-% titanium dioxide, and about 0.01 wt-% to about 0.10 wt-% iron oxide, based on the total weight of the polymeric coating material, give a natural tooth enamel appearance to the coating. Additional pigments or colorants can be optionally added to the starting coating powders to color-match the polymeric coating to a desired tooth color.

Optional additives that can be included in the coating powders include fillers, for example. Filler material can be used to enhance the durability and wear time of the polymer-coated crowns. Fillers may be selected from one or more of any material suitable for incorporation into a starting coating powder for use in preparing an aesthetic polymer coated crown. The filler is finely divided and preferably has a maximum particle size (preferably, diameter) of less than about 50 microns and an average particle size (preferably, diameter) of less than about 10 microns. The filler can have a unimodal or polymodal (e.g., bimodal) particle size distribution. The filler can be an inorganic material or a crosslinked organic material that is optionally filled with inorganic filler. The filler should in any event be of low toxicity and suitable for use in the mouth as part of a dental crown polymeric coating.

Examples of suitable inorganic fillers are naturally occurring or synthetic materials such as quartz, nitrides (e.g., silicon nitride), glasses derived from, for example Ce, Sb, Sn, Zr, Sr, Ba and Al, silica, feldspar, borosilicate glass, kaolin, talc, titania, and zinc glass. Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169 (Randklev). Metallic fillers may also be incorporated, such as particulate metal filler made from pure metal or metal alloys.

The amount of filler used is sufficient to enhance the durability and/or wear time of a crown polymeric coating, for example, to eliminate or reduce the loss of coating (e.g., by delamination, flaking off, or wearing off) during typical crimping and trimming manipulations of the crown or during the very long wear times (preferably during the lifetime of the patient) of the crowns. Preferably, filler material (i.e., one or more types of fillers) is used in an amount of at least about 0.5 wt-%, and more preferably at least about 2 wt-%, based on the total weight of the coating powder. Preferably, filler material is used in an amount of no greater than about 9 wt-%, and more preferably no greater than about 4 wt-%, based on the total weight of the coating powder.

Preferred fillers are silica-based fillers. Preferred silica particles have an average particle size (preferably, diameter) of less than about 200 nanometers (nm); more preferably, the particles are less than about 100 nm in average particle size (preferably, diameter). These measurements are preferably based on a TEM (transmission electron microscopy) method, whereby a population of particles is analyzed to obtain an average particle size. The average surface area of the silica particles is preferably greater than about 15 $m^2/g$; more preferably greater than about 30 $m^2/g$.

Preferred nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327, and 2329. Silica-based fillers including non-aggregated silica filler particles and methods of preparing the fillers are disclosed in, for example, International Publication Nos. WO 01/30304 (Wu et al.), WO 01/30305 (Zhang et al.), WO 01/30306 (Windisch et al.), and WO 01/30307 (Zhang et al.).

Optionally, fumed silica can be included in the coating powders. Suitable fumed silicas include, for example, products sold under the tradename AEROSIL series OX-50, -130, -150, and -200 available from DeGussa AG, (Hanau, Germany), and CAB-O-SIL M5 available from Cabot Corp (Tuscola, Ill.).

The silica particles optionally present as fillers in the starting coating powders are preferably surface treated, for example, with silane treatment agents. Such surface modifying agents can enhance the compatibility of the fillers with other ingredients in the coating powders. Typical silane treatment agents with polymerizable groups include γ-methacryloxylpropyltrimethoxysilane, available commercially under the trade designation A-174 from Witco OSi Specialties (Danbury, Conn.) and γ-glycidoxypropyltrimethoxy silane, a product available under the trade designation G6720 from United Chemical Technologies (Bristol, Pa). Other surface modifying agents that do not contain polymerizable groups can be included in the coating powders. Examples of silane treatment agents of this type include, for example, alkyl or aryl polyethers, alkyl, hydroxy alkyl, hydroxy aryl, and amino alkyl functional silanes. Alternatively, a combination of surface modifying agents can be used.

Other optional additives that can be included in the polyester/epoxy hybrid coating powders include crosslinkers, curing agents, extenders, flow aids, and combinations thereof. Typical crosslinkers and curing agents include, for example, amines, anhydrides, blocked isocyanates, melamines, and glycidyl-based compounds.

The starting coating powders are prepared by combining the powder components using conventional techniques. For example, the polyester/epoxy hybrid component resins (i.e., a polyester resin and an epoxy polymer resin) can be heated to a molten state, blended with an appropriate pigment or combination of pigments and other optional additives (e.g., fillers), and allowed to cool. This mixture is then ground to a fine powder. Additionally or alternatively, for example, optional pigments and/or fillers can be blended into a dry polyester/epoxy hybrid coating powder, preferably, to form a homogeneous coating powder blend. Desirably, the particle size of the coating powders is sufficient to allow for the use of powder coating techniques. Preferably, the average particle size of the coating powders is at least about 20 microns and no greater than about 100 microns.

The polymeric coating is directly applied to the stainless steel crown. A typical procedure for coating a preformed stainless steel crown involves conventional powder coating techniques, such as electrostatic spraying processes, followed by thermally treating the powder to melt the powder coating and bond the resulting molten material to the crown surface. Such powder coating techniques are well known to one of skill in the art.

In a preferred embodiment, the stainless steel crown is grounded and the powder is charged with a negative charge such that the sprayed particles are electrostatically attracted to and adhered to the surface of the crown. Following spraying, the powder-coated crown is heated at a temperature and for a time sufficient to melt, cure, and fuse the particles to the stainless steel. Preferably, this is for about 18–22 minutes, and most preferably about 20 minutes, at a temperature above the melting or softening point of the polyester/epoxy composition. Preferably, the temperature is about 180° C. to about 200° C., and more preferably about 190° C., during which time the powder coating becomes molten and bonds to the metal surface.

EXAMPLES

The following examples are given to illustrate, but not limit, the scope of this invention. Unless otherwise indicated, all parts and percentages are by weight and all molecular weights are weight average molecular weight.

Test Methods

Crimping and Trimming

Polymer coated stainless steel crowns were crimped and trimmed as generally described on page 5 of the 3M Prefabricated Crowns User Guide, Technical Service Publication No. 70-2008-7866-1, 1996, available from 3M Company, St. Paul, Minn. The lingual edge of each crown was trimmed using crown scissors (No. 801-202, 3M Company), and the buccal and lingual edges were crimped using crimping pliers (No. 800-421, 3M Company). Visual observation of any coating damage, e.g., cracking, chipping, flaking, delamination, was made and reported following the crimping and trimming of each coated crown.

Toothbrush Abrasion

This test was designed to utilize a simulated toothbrushing machine to measure the coating wear of various powder-coated stainless steel discs 0.75 inch (1.9 cm) in diameter and 0.0073 inch (0.19 mm) thick. The discs were die-cut from AISI-Type 305 stainless steel sheeting (based on the American Iron and Steel Institute Classification of Chromium-Nickel Stainless Steels). A split sample design was used such that one-half of each disc surface was covered with tape and unbrushed and the other half was uncovered and brushed.

The simulated toothbrushing machine was a DC Servo Toothbrushing Simulator (University of Minnesota Dental Research Center for Biomaterials and Biomechanics; Dynamic Systems, Elk River, Minn.) and had a toothbrush head applied against the samples at a predetermined and controlled force of 1 Newton. The machine was operated at a frequency of +0.5 Hz and at an amplitude of 20 mm. The test toothbrush was a Colgate Number 32 Child's toothbrush (Colgate-Palmolive Co., N.Y., N.Y.) and the toothpaste used was CREST Regular Paste Tarter Protection (Proctor & Gamble, Cincinnati, Ohio). For each test, brushing was run for 30 cycles (one minute), the brush recharged with paste and run another 30 cycles (one minute), and then the brush recharged with paste and run a final 30 cycles (one minute).

At the conclusion of each test, the brushed and unbrushed sides of the disc were compared in a laser reflectometer equipped with a positioning table (Parker Hannifin Co, Irwin, Pa.) and a laser (Newport Co., Irvine, Calif.). The difference between reflectometer values of brushed and unbrushed sides was reported as a percent loss of reflectance (i.e., gloss or shine) and was considered to be a measure of early loss of coating material.

Two-Body Wear ("Artificial Mouth" Model)

This test was designed to utilize a Servo-Hydraulic Model of the "Artificial Mouth" (University of Minnesota Dental Research Center for Biomaterials and Biomechanics; MTS Corporation, Minneapolis, Minn.) to measure the coating wear of various powder-coated metal dental crowns. The "Artificial Mouth" Model is designed to simulate chewing action and is described in R. Delong and W. H. Douglas, "The Development of an Artificial Oral Environment of Testing of Restoratives," J. Dental Research, No. 62, Pages 32–36, 1983. The "Artificial Mouth" Model was configured such that the test coated crown sample (maxillary central) was opposed by a bovine enamel tooth (mandibular cuspid). During the test run, the bovine enamel tooth would slide against the labial surface of the coated crown at 6 Newtons force and at one cycle per second. The test was stopped after every 500 cycles and the point of contact on the coated crown (lingual surface) was photographed with a high-resolution digital camera. The test was then continued for a total of 5000 cycles. The resulting digital photographs were closely scrutinized and rated on the basis of the features of the wear area and on the degree of penetration of the coating (that is clearly visible due to the underlying exposed metal crown). The photograph assessments were rated according to the following scale:

1. Evasive visible metal exposure
2. Medium visible metal exposure
3. Minimum visible metal exposure
4. Minimum visible coating surface wear (no visible metal exposed)
5. No visual wear Powder Coating Process The polymer coated stainless steel dental crowns of the present invention were prepared utilizing a conventional powder coating method for painting a metal surface by electrostatically spraying a coating powder onto the metal surface and then heating until the powder becomes molten and bonds to the surface. Such powder coating methods have been described previously in the literature, e.g., in Powder Coating, Second Edition, published by The Powder Coating Institute, 1999.

For the present invention, a stainless steel article, e.g., a stainless steel dental crown or a stainless still disc for performance evaluations, was prepared for coating by cleaning with acetone and drying. Optionally, the metal surface was fine-bead or sandblasted prior to the acetone cleaning.

The coating powder was added to a VERSA-SPRAY II IPS electrostatic spray gun (Nordson Corp., Amherst, Ohio) and sprayed onto the metal part that had been grounded to a movable conveyer belt. The spray gun imparted a negative charge to the powder particles such that the particles were electrostatically attracted to and adhered to the grounded metal part. Following spraying, the coated metal part was conveyed into an oven for about 20 minutes at 375° F. (1 90° C.), during which time the powder coating melted and bonded to the metal surface. The coated metal part was then cooled to room temperature. Typically, the resulting layer of coated polymer on the metal part had a thickness of 0.002 to 0.003 inch (50 to 75 microns).

Starting Coating Powders

Powder I

Powder I was a white polyester-epoxy hybrid coating powder available as CORVEL FDA WHITE 40-1242 from Morton Powder Coatings, Reading, Pa. The powder could be tinted by heating to a molten state, blending in an appropriate pigment or combination of pigments, cooling, and grinding the resulting solid into a fine powder. For these Examples, the powder used was untinted (i.e., with no additional pigments added). Optionally, added filler material was blended into the powder. The optional filler materials used were Zr—Si (silane-treated Zirconia-Silica filler prepared as described in U.S. Pat. No. 6,030,606 (Holmes)), AEROSIL OX-50 (Degussa Corp., Akron, Ohio), and Silica A (silane-treated silica particles having an avenge particle size of about 20 microns prepared as described for Filler C in U.S. patent application Ser. No. 09/428,937 (Zhang, et al.) (abandoned in favor of U.S. patent application Ser. No. 10/122,767, now published as US 2002-0156152 A1). Powder I, with or without added filler, was subsequently utilized to powder coat stainless steel articles.

Powder II

Powder IIA (light ivory color) and Powder IIB (medium ivory color) were polyester-epoxy hybrid coating powders available as Product No. 388170B (Light Ivory) and Product No. 388171B (Dark Ivory), respectively, from Dupont, Wilmington, Del. Optionally, added filler material was blended into the powders. Powder IIA and Powder IIB, with or without added filler, were subsequently utilized to powder coat stainless steel articles.

Powder III

Powder III was an almond-colored epoxy-based coating powder available as CORVEL EPOXY 10-1008 from Morton Powder Coatings. Optionally, added filler material was blended into the powder. Powder III, with or without added filler, was subsequently utilized to powder coat stainless steel articles.

Examples 1–15

Stainless Steel Crowns with Polymeric Polyester-Epoxy Hybrid Coating

Polished stainless steel crowns (3M Company) were cleaned with acetone and then powder coated with a polyester-epoxy hybrid powder utilizing the Powder Coating Process described herein. The starting crowns and powders utilized are shown in Table 1 with the resulting polymeric coated crowns (Examples 1–15) all having a hard, smooth, white or tinted, aesthetically pleasing appearance.

TABLE 1

Polymer Coated Stainless Steel Crowns

| Example | Stainless Steel Crown Description (3M Product No.) | Powder | Added Filler (Wt.-%) | Coated Crown Color |
|---|---|---|---|---|
| 1 | Anterior (907012) | I | No Filler | White |
| 2 | Posterior (D-LR-3) | I | No Filler | White |
| 3 | Anterior (907012) | I | 4% OX-50 | White |
| 4 | Posterior (D-LR-3) | I | 4% OX-50 | White |
| 5 | Anterior (907012) | I | 8% OX-50 | White |
| 6 | Posterior (D-LR-3) | I | 8% OX-50 | White |
| 7 | Anterior (907012) | I | 4% Silica A | White |
| 8 | Posterior (D-LR-3) | I | 4% Silica A | White |
| 9 | Anterior (907012) | I | 8% Silica A | White |
| 10 | Posterior (D-LR-3) | I | 8% Silica A | White |
| 11 | Anterior (907022) | I | No Filler | White |
| 12 | Anterior (907004) | IIA | No Filler | Light Ivory |
| 13 | Anterior (907004) | IIB | 2% Zr—Si | Medium Ivory |
| 14 | Anterior (907004) | IIB | 5% Zr—Si | Medium Ivory |
| 15 | Anterior (907004) | IIB | 7% Zr—Si | Medium Ivory |
| CE-1 | Anterior (907004) | III | No Filler | Almond |

Comparative Example 1

Stainless Steel Crowns with Polymeric Epoxy Coating

Stainless steel crowns (3M Company) were prepared and then powder coated with an epoxy powder utilizing the Powder Coating Process described herein. The starting crowns and powders utilized are shown in Table 1 with the resulting coated crowns (Comparative Example 1 (CE-1)) all having a hard, smooth, almond-colored appearance.

Test Evaluations and Results

Evaluation of Staining

The objective of this evaluation was to determine if polymeric hybrid coated stainless steel crowns would stain when subjected to various challenges over a period of time at elevated temperature.

Five different staining solutions were prepared and consisted of the following materials: Staining Solution A (distilled water, a control); Staining Solution B (16% carbamide peroxide whitener gel from 3M Company); Staining Solution C (COCA COLA CLASSIC); Staining Solution D (50150 HEINZ Mustard/ HEINZ Ketchup), and Staining solution E (a coffee-tea-grape juice solution prepared by boiling 200 ml grape juice concentrate containing 30 g ground coffee and 3 tea bags, followed by cooling and decanting of the liquid).

Three small hybrid-coated stainless steel crowns (Example 11, initially white in color) were submersed in each of the five different staining solutions (at 37° C.) and then removed at 1 day, 4 days, 7 days, and 14 days for visual inspection. For each inspection, the crowns were removed from the staining solutions, rinsed thoroughly with water, dried, visually inspected, and then returned to the 37° C. solutions. Results are provided in Table 2 and show that the only significant staining observed was a light yellow coloring of the crowns from Staining Solution D.

TABLE 2

Staining Results of Polymer Coated Stainless Steel Crowns

| Staining Solution | Day Inspected | Crown Appearance |
|---|---|---|
| A (Distilled Water) | 1, 2, 7, 14 | White (All Days) |
| B (Peroxide Whitener) | 1, 2, 7, 14 | White (All Days; increased whiteness at Day 14) |
| C (COCA-COLA) | 1 | Very slight off-color |
|  | 2 | Very slight off-color |
|  | 7 | Slight off-color |
|  | 14 | Slight off-color |
| D (Mustard/Ketchup) | 1 | Very light yellow |
|  | 2 | Light yellow |
|  | 7 | Light yellow |
|  | 14 | Light yellow |
| E (Coffee/Tea/Grape Juice) | 1, 2, 7, 14 | Slight off-color (All Days) |

Crimping and Trimming

The polymeric hybrid-coated stainless steel crowns were evaluated for coating effects following practical handling manipulations as described in the Crimping and Trimming Test Method described herein. The resulting visual observations are reported in Table 3 and show that the hybrid-coated crowns of the present invention (Examples 1–9 and 12–15) generally showed little or no significant cracking or flaking. In contrast, crimping of the comparative epoxy-coated stainless steel crown resulted in immediate and significant separation of the coating from the crown surface.

TABLE 3

Crimping and Trimming Observations of Polymer-Coated Stainless Steel Crowns

| Coated Crown Example | Powder | Added Filler (Wt.-%) | Crimping Observations | Trimming Observations |
|---|---|---|---|---|
| 1 | I | No Filler | OK[a] | OK |
| 2 | I | No Filler | OK | OK |
| 3 | I | 4% OX-50 | OK | OK |
| 4 | I | 4% OX-50 | OK | OK |
| 5 | I | 8% OX-50 | Little Chipping | OK |
| 6 | I | 8% OX-50 | Cracked | Chipped |
| 7 | I | 4% Silica A | Slight Cracking | Delamination |
| 8 | I | 4% Silica A | Slight Chipping | OK |
| 9 | I | 8% Silica A | Slight Cracking | OK |
| 12 | IIA | No Filler | OK | OK (Difficult to cut; attributed to small crown size) |
| 13 | IIB | 2% Zr—Si | OK (Metal surface shown through after crimping) | OK |
| 14 | IIB | 5% Zr—Si | OK | OK |
| 15 | IIB | 7% Zr—Si | OK | OK |
| CE-1 | III | No Filler | Immediate and significant separation of coating from metal | Slight cracking |

[a]OK designation means that no cracking or flaking of the coating was observed.

Toothbrush Abrasion

Polymeric hybrid-coated stainless steel discs were evaluated for coating wear as described in the Toothbrush Abrasion Test Method described herein. The discs were cleaned with acetone and then powder coated with a polyester-epoxy powder utilizing the Powder Coating Process described herein. The powders utilized and the results of the Toothbrush Abrasion Test are shown in Table 4. It can be concluded from these results that the addition of filler material to the coating powder increased the amount of coating wear on the coating discs as measured by percent loss of reflection.

TABLE 4

Toothbrush Abrasion Test Results of Polymer Coated Stainless Steel Discs.

| Run | Powder | Added Filler to Powder | Reflection Value Unbrushed | Reflection Value Brushed | Percent Loss of Reflection |
|---|---|---|---|---|---|
| 1 | I | 4% OX-50 | 228 | 77.4 | 66 |
| 2 | I | 4% Silica A | 205 | 141 | 31 |
| 3 | I | 8% Silica A | 111 | 47.1 | 58 |
| 4 | I | 8% Silica A[a] | 142 | 56.3 | 60 |
| 5 | I | No Added Filler | 272 | 220 | 19 |

[a]Disc bead blasted prior to acetone cleaning and subsequent powder coating.

Two-Body Wear

Polymer coated stainless steel crowns were evaluated for coating wear as described in the Two-Body Test Method described herein. The testing results for Example 1; Comparative Example 1; and two commercial coated crowns, PEDO PEARLS (a polyester/epoxy hybrid coated aluminum crown, Pedo Pearls, Murlin, Oreg.) and WHITE STEEL (an epoxy polymer coated stainless steel crown, White Steel Dental Products, Murphy, Oreg.) are shown in Table 5. Although these results are inconclusive to provide suitable comparisons, the polyester/epoxy hybrid-coated crown of the present invention demonstrated good durability.

TABLE 5

Two-Body Wear Test Results of Polymer Coated Metal Crowns.

| Coated Crown Tested | Coated Crown Description | Initial | 500 Cycles | 1000 Cycles | 5000 Cycles |
|---|---|---|---|---|---|
| Example 1 | Hybrid Coated SS | 5 | 4 | 3 | 3 |
| Comp. Ex. 1 | Epoxy Coated SS | 5 | 4 | 3 | NA |
| PEDO PEARLS | Hybrid Coated Al | 5 | 3 | NA | 2 |
| WHITE STEEL | Epoxy Coated SS | 5 | NA[a] | NA | 1 |

[a]NA = Not Available (Photograph not taken at this number of cycles).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A dental crown comprising a stainless steel shell sized to cover a tooth portion of a patient and a polymeric coating covering at least a portion of the outer surface of the stainless steel shell, wherein the polymeric coating comprises a polyester/epoxy hybrid composition that includes a blend of a polyester resin and an epoxy resin.

2. The dental crown of claim 1 wherein the polymeric coating further comprises a pigment.

3. The dental crown of claim 2 wherein the pigment is selected from the group consisting of titanium dioxide, iron oxide, and mixtures thereof.

4. The dental crown of claim 1 wherein the polymeric coating further comprises a filler.

5. The dental crown of claim 4 wherein the filler comprises silica.

6. The dental crown of claim 5 wherein the silica is silane treated.

7. A dental crown comprising a stainless steel shell sized to cover a tooth portion of a patient and a polymeric coating covering at least a portion of the outer surface of the stainless steel shell, wherein the polymeric coating comprises a polyester/epoxy hybrid composition that includes a blend of a polyester resin and an epoxy resin, and wherein the coating is at least about 35 microns thick.

8. The dental crown of claim 7 wherein the polymeric coating further comprises a pigment.

9. The dental crown of claim 8 wherein the pigment is selected from the group consisting of titanium dioxide, iron oxide, and mixtures thereof.

10. The dental crown of claim 7 wherein the polymeric coating further comprises a filler.

11. The dental crown of claim 10 wherein the filler comprises silica.

12. The dental crown of claim 11 wherein the silica is silane treated.

13. A dental crown comprising a stainless steel shell sized to cover a tooth portion of a patient and a polymeric coating covering at least a portion of the outer surface of the stainless steel shell, wherein the polymeric coating comprises a polyester/epoxy hybrid composition that includes a blend of a polyester resin and an epoxy resin, a pigment, and a filler, and wherein the coating is at least about 35 microns thick.

14. The dental crown of claim 13 wherein the filler comprises silica.

15. The dental crown of claim 14 wherein the silica is silane treated.

16. A method of coating a stainless steel crown, the method comprising:
    providing a stainless steel shell sized to cover a tooth portion of a patient;
    providing a polyester/epoxy hybrid powder that includes a blend of a polyester resin and an epoxy resin; and
    applying the powder to at least a portion of the outer surface of the stainless steel shell to form a polymeric coating.

17. The method of claim 16 further comprising heating the powder-coated shell at a temperature and for a time sufficient to melt and fuse the powder to the stainless steel shell.

18. The method of claim 16 wherein the powder has an average particle size of about 20 to about 100 microns.

19. The method of claim 16 wherein the coating is at least about 35 microns thick.

20. A dental crown prepared by the method of claim 16.

* * * * *

UNITED STATES PATENT AND TRADEMARK OFFICE
CERTIFICATE OF CORRECTION

PATENT NO. : 7,008,229 B2
APPLICATION NO. : 10/121941
DATED : March 7, 2006
INVENTOR(S) : William J. Stoller It is certified that error appears in the above-identified patent and that said Letters Patent is hereby corrected as shown below:

Page 2, Col. 1 (Other Publications)
Line 11, Delete "Inc" and insert -- Inc. --, therefor.
Line 19, Delete "www.pedopearls.com.index." and insert
--www.pedopearls.com/index. --, therefor.

Page 2, Col 2 (Other Publications)
Line 2, Delete "www.pedopearls.com.contact.html" and insert
-- www.pedopearls.com/contact.html --, therefor.

Column 3
Line 65, Delete "Minn.." and insert -- Minn. --, therefor.

Column 8
Line 61, After "wear" insert -- . --.

Column 9
Line 20, Delete "1 90°" and insert -- 190°--, therefor.
Line 42 (Approx.), Delete "Ohio)" and insert -- Ohio.) -- ; therefor.
Line 43 (Approx.), Delete "avenge" and insert -- average --, therefor.
Line 45 (Approx.), After "(Zhang, et al.)" insert --) --.

Column 10
Line 59 (Approx.), Delete "50150" and insert --50/50 --, therefor.

Column 11
Line 65, Delete ""[a]OK" and insert -- [a]-OK --, therefor.

UNITED STATES PATENT AND TRADEMARK OFFICE
CERTIFICATE OF CORRECTION

PATENT NO. : 7,008,229 B2
APPLICATION NO. : 10/121941
DATED : March 7, 2006
INVENTOR(S) : William J. Stoller It is certified that error appears in the above-identified patent and that said Letters Patent is hereby corrected as shown below:

Column 12
Line 32, Delete ""$^a$Disc" and insert -- $^a$-Disc --, therefor.
Line 64, Delete ""$^a$NA" and insert -- $^a$-NA --, therefor.

Signed and Sealed this

Sixteenth Day of January, 2007

JON W. DUDAS
*Director of the United States Patent and Trademark Office*